(12) United States Patent
Dussarrat et al.

(10) Patent No.: US 8,668,957 B2
(45) Date of Patent: *Mar. 11, 2014

(54) METHOD OF FORMING DIELECTRIC FILMS, NEW PRECURSORS AND THEIR USE IN SEMICONDUCTOR MANUFACTURING

(75) Inventors: Christian Dussarrat, Tokyo (JP); Nicolas Blasco, Grenoble (FR); Audrey Pinchart, Toulouse (FR); Christophe Lachaud, Saint Michel sur Orge (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 1322 days.

This patent is subject to a terminal disclaimer.

(21) Appl. No.: 12/303,169

(22) PCT Filed: Mar. 16, 2007

(86) PCT No.: PCT/EP2007/052507

§ 371 (c)(1),
(2), (4) Date: Apr. 3, 2009

(87) PCT Pub. No.: WO2007/141059

PCT Pub. Date: Dec. 13, 2007

(65) Prior Publication Data

US 2009/0203222 A1    Aug. 13, 2009

(30) Foreign Application Priority Data

Jun. 2, 2006  (WO) ................. PCT/EP2006/062893

(51) Int. Cl.
*C23C 16/40*  (2006.01)

(52) U.S. Cl.
USPC ............ 427/255.31; 427/255.28; 427/255.33; 427/255.34; 427/255.36; 427/255.394

(58) Field of Classification Search
None
See application file for complete search history.

(56) References Cited

U.S. PATENT DOCUMENTS

| | | | |
|---|---|---|---|
| 5,527,752 A | 6/1996 | Reichle et al. | |
| 5,846,895 A | 12/1998 | Gila et al. | |
| 5,861,352 A | 1/1999 | Gila et al. | |
| 6,001,742 A | 12/1999 | Chang | |
| 6,197,683 B1 | 3/2001 | Kang et al. | |
| 6,268,448 B1 | 7/2001 | Collins et al. | |
| 6,445,023 B1 | 9/2002 | Vaartstra et al. | |
| 6,548,424 B2 | 4/2003 | Putkonen | |
| 6,669,990 B2 | 12/2003 | Min et al. | |
| 6,689,675 B1 | 2/2004 | Parker et al. | |
| 6,743,473 B1 | 6/2004 | Parkhe et al. | |
| 6,844,271 B2 * | 1/2005 | Loftin et al. ................. | 438/785 |
| 6,858,547 B2 | 2/2005 | Metzner et al. | |
| 6,984,591 B1 | 1/2006 | Buchanan et al. | |
| 7,108,747 B1 | 9/2006 | Leskala et al. | |
| 2001/0001949 A1 | 5/2001 | Westmoreland et al. | |
| 2004/0235312 A1 | 11/2004 | Loftin et al. | |
| 2005/0056219 A1 | 3/2005 | Dip et al. | |
| 2005/0260357 A1 | 11/2005 | Olsen et al. | |
| 2006/0062910 A1* | 3/2006 | Meiere ........................ | 427/226 |
| 2006/0062917 A1 | 3/2006 | Muthukrishnan et al. | |
| 2006/0097305 A1 | 5/2006 | Lee | |
| 2006/0228888 A1 | 10/2006 | Lee et al. | |
| 2008/0308793 A1 | 12/2008 | Jeong et al. | |
| 2009/0203222 A1* | 8/2009 | Dussarrat et al. ............ | 438/778 |
| 2009/0311879 A1* | 12/2009 | Blasco et al. ................ | 438/785 |

FOREIGN PATENT DOCUMENTS

| | | |
|---|---|---|
| EP | 1 067 595 | 1/2001 |
| EP | 1 524 299 | 4/2005 |
| JP | 2001 102326 | 4/2001 |
| JP | 2001 355070 | 12/2001 |
| JP | 2002 069641 | 3/2002 |
| JP | 2002 093803 | 3/2002 |
| JP | 2002 093804 | 3/2002 |
| JP | 2004 300579 | 10/2004 |
| JP | 2004 349710 | 12/2004 |
| JP | 2005 104994 | 4/2005 |
| JP | 2005 171291 | 6/2005 |
| JP | 2005 209766 | 8/2005 |
| WO | WO 96 27032 | 9/1996 |
| WO | WO 97 49105 | 12/1997 |
| WO | WO 02 18394 | 3/2002 |

| | | |
|---|---|---|
| WO | WO 03 035926 | 5/2003 |
| WO | WO 2004 010469 | 1/2004 |
| WO | WO 2005 113852 | 12/2005 |
| WO | WO 2006 131751 | 12/2006 |
| WO | WO 2007 005088 | 1/2007 |
| WO | WO 2007 011973 | 1/2007 |
| WO | WO 2007 030673 | 3/2007 |
| WO | WO 2007 066546 | 6/2007 |
| WO | WO 2007 140813 | 12/2007 |
| WO | WO 2007 141059 | 12/2007 |
| WO | WO 2009 106433 | 9/2009 |

OTHER PUBLICATIONS

Gordon et al.; Surface Morphology and Crystallinity Control in the Atomic Layer Deposition (ALD) of Hafnium and Zirconium Oxide Thin Films; Journal of Crystal Growth; 249, 251-261; 2003.*
Schneider, H. et al. "Immobilization of $\eta^5$-cyclopentadienyltris(dimethylamido)zirconium polymerization catalysts on a chlorosilane- and HMDS-modified mesoporous silica surface: A new concept for supporting metallocene amides towards heterogenous single-site-catalysts," Journal of Molecular Catalysts A; Chemical 170 (2001) pp. 127-141.
Carta, G. et al., "Thermal properties of volatile organohafnium precursors for $HfO_2$ MOCVD processes," Electrochemical Society Proceedings vol. 2005-09, pp. 260-267.
Caymax, M. et al., "High-k materials for advanced gate stack dielectrics: a comparison of ALCVD and MOCVD as deposition technologies," 2003 Materials Research Society Symposium Proceedings, vol. 765, pp. 47-58.
Chang, H.S. et al. "Electrical and physical properties of $HfO_2$ deposited via ALD using $Hf(OtBu)_4$ and ozone atop $Al_2O_3$." Electrochem. Solid-State Letters, 7 (6) F42-F44 (2004).
Cotton, S.A., "Ti, Ar, Hf," Annu. Rep.Prog. Chem., Sect. A: Inorganic Chemistry, 1993, 90, pp. 119-130.
Hausmann, D.M. et al. "Atomic layer deposition of hafnium and zirconium oxide using metal amide precursors." Chem., Mater, 2002, 14, 4350-4353.
Juppo, M. et al. "In situ mass spectrometry study on surface reactions in atomic layer deposition of $Al_2O_3$ thin films from trimethylaluminum and water." Langmuir 2000, 16, pp. 4034-4039.
Kawahara, T. et al. "Effect of Hf source, oxidizing agents, and $NH_3$/Ar plasma on the properties of $HfAlO_x$ films prepared by atomic layer deposition." J. Appl. Phys., vol. 43, No. 7A, 2004, pp. 4129-4134.
Kim, M-S et al., "ALD analyses of HfCl4 + O3 and HfCl4 + H2O by mass spectroscopy," Electrochemical Society Proceedings vol. 2005-05, pp. 397-403.
Kukli, K. et al., "Atomic layer deposition of hafnium dioxide films from 1-methoxy-2-methyl-2-propanolate complex of hafnium," Chem Mater. 2003, 15, pp. 1722-1727.
Lehn, J-S et al., "New precursors for the DVD of zirconium and hafnium oxide films," Chem Vap. Deposition 2006, 12, pp. 280-284.
Niinisto, J. et al. "In situ quadrupole mass spectrometry study of atomic-layer deposition of $ZrO_2$ using $Cp_2Zr(CH_3)_2$ and water." Langmuir, 7321, 21, 2005.
Potter, R.J. et al., "Deposition of $HfO_2$, $Gd_2O_3$ and $PrO_x$ by liquid injection ALD techniques," Chem. Vap. Deposition 2005, 11, No. 3, pp. 159-169.
Putkonen, M. et al. "Zirconia thin films by atomic layer epitaxy. A comparative study on the use of novel precursors with ozone." J. Mater. Chem., 3141, 11, 2001.
Ritala, M. et al., "Atomic Layer Deposition," Ch. 2, Handbook of Thin Film Materials, H.S. Nalwa, ed., vol. 1, "Deposition and Processing of Thin Films," Academic Press, San Diego, CA, 2002.
Senzaki, Y. et al. "Atomic layer deposition of hafnium oxide and hafnium silicate thin films using liquid precursors and ozone." J. Vac. Sci. Technol. A 22(4), Jul./Aug. 2004.
Triyoso, D.H. et al. "Physical and electrical characteristics of $HfO_2$ gate dielectrics deposited by ALD and MOCVD," J. Electrochem, Soc., 152 (3) G203-G209 (2005).
Williams, P.A. et al., "Novel mononuclear alkoxide precursors for the MOCVD of ZrO2 and HfO2 thin films," Chem Vap. Deposition 2002, 8, No. 4, pp. 163-170.
Written Opinion for corresponding PCT/EP2006/052507, Oct. 31, 2007.
Written Opinion for related PCT/EP2006/062893, Sep. 27, 2007.
International Search Report and Written Opinion for related PCT/EP2009/051683, May 14, 2009.
Becker et al., "Atomic Layer Deposition of Hafnium and Zirconium Nitrides", Chem. Mater. 2004, 16, 3497-3501.
Cano et al., "Neutral and Cationic [Bis(n1-amidosilyl)-n5-cyclopentadienyl]titanium and—zirconium Complexes: Synthesis, X-ray Molecular Structures and DFT Calculations", Eur. J. Inorg. Chem. 2003 2463-2474.
Ciruelo et al., "Synthesis and reactivity of new silyl substituted monocyclopentadienyl zirconium complexes. X-ray molecular structure of $[Zr(N^5-C_5H_4(SiMe_2CH_2Ph))(CH_2Ph)_3]$", Journal of Organometallic Chemistry 547 (1997) 287-296.
Irigoyen et al., Synthesis and Characterization of chlorobis(dialkylamido) and alkylbis(dialkylamido) derivatives of $[(n^5-C_5Me_5)MCl_3](M=Ti, Zr)$, Journal of Organometallic Chemistry, 494 (1995) 255-259.
Jutzi et al., "Halbsandwich-Komplexe der Elemente Titan und Zirconium mit dem (Diisopropylaminoethyl) cyclopentadienyl-Ligand: Molekülstruktur von $[(C_5H_4CH_2CH_2N(H)^iPr_2)ZrCl_3]^+Cl^- \cdot 2CH_3OH$", Journal of Organometallic Chemistyr 533 (1997), 237-245.
Niinistö et al., "Development of Novel Processes for Atomic Layer Deposition of High-k Dielectrics", $72^{nd}$ Annual Meeting of the DPG, Feb. 27, 2008, Berlin.
Pinchart et al., "Novel Thermally-Stable Hafnium and Zirconium ALD Precursors", IEEE/SEMI Advanced Semiconductor Manufacturing Conference (ASMC) 2007.
Rogers et al., "Fulvene to Cyclopentadienyl Conversion with Homoleptic Complexes of Zirconium and Hafnium", Organometallics 1999 18, 3976-3980.
Schneider et al., "Immobilization of n5-cyclopentadienyltris(dimethylamido)zirconium polymerization catalysts on a chlorosilane- and HMDS-modified mesoporous silica surface: a new concept for supporting metallocene amides towards heterogenous single-site-catalysts", Journal of Molecular Catalysis A: Chemical 170 (2001) 127-141.
Winter, C.H. et al., "Metallic Materials Deposition: Metal-organic Precursors," Encyclopedia of Inorganic Chemistry, 2006, John Wiley & Sons Ltd., DOI: 10.1002/0470862106.ia138.
Vollmerhaus, R. et al., "Synthesis and structure of Group 4 iminophosphonamide complexes," Organometallics, 2005, vol. 24, pp. 494-507.
International Search Report for PCT/EP2007/052507, May 21, 2007.
International Search Report for PCT/EP2006/062893, Nov. 9, 2006.
Codato, S., et al. "MOCVD growth and characterization of $ZrO_2$ thin films obtained from unusual organo-zirconium precursors." Chemical Vapor Deposition, Wiley-VCH Verlag, Weinheim, Germany, vol. 11, No. 11, 1999, pp. 159-164.
Chandra, G. et al. "Amido-derivatives of metals and metalloids. Part VI. Reactions of titanium(IV), zirconium(IV), and hafnium(IV) amides with protic compounds." Journal of Chemical Society (A), 1968, pp. 1940-1945.
Herrmann, W.A. et al., "Volatile metal alkoxides according to the concept of donor functionalization," Angewandte Chemie International Edition in English, (1995) vol. 34, pp. 2187-2206.
Kukli, K. et al., "Influence of growth temperature on properties of zirconium dioxide films grown by atomic layer deposition," Journal of Applied Physics, Aug. 15, 2002, vol. 92, No. 4, p. 1833-1840.
Putkonen, M. et al., "Organometallic precursors for atomic layer deposition," Topics in Organometallic Chemistry (2005) pp. 125-145.
Rie, K.-T. et al., "Plasma assisted CVD for low temperature coatings to improve the wear and corrosion resistance," Surface and Coatings Technology (1996) vol. 86-87, pp. 498-506.

* cited by examiner

*Primary Examiner* — Curt Mayes
*Assistant Examiner* — Guinever Gregorio
(74) *Attorney, Agent, or Firm* — Patricia E. McQueeney

(57) ABSTRACT

Method of deposition on a substrate, of a metal containing dielectric film comprising a compound of the formula (I):

$$(M^1_{1-a}M^2_a)O_bN_c, \qquad (I)$$

wherein $0 \leq a < 1$, $0 < b \leq 3$, $0 \leq c \leq 1$, $M^1$ represents a metal selected from (Hf), (Zr) and (Ti); and $M^2$ represents a metal atom atoms, which comprises the following steps:

A step a) of providing a substrate into a reaction chamber;

A step (b) of vaporizing a $M^1$ metal containing precursor of the formula (II):

$$(R^1_yOp)_x(R^2_tCp)_zM^1R'_{4-x-z} \qquad (II)$$

wherein $0 \leq x \leq 3$, preferably $x=0$ or 1, $0 \leq z \leq 3$, preferably $z=1$ or 2, $1 \leq (x+z) \leq 4$, $0 \leq y \leq 7$, preferably $y=2$ $0 \leq t \leq 5$, preferably $t=1$, $(R^1_yOp)$ represents a pentadienyl ligand, which is either unsubstituted or substituted; $(R^2_tCp)$ represents a cyclopentadienyl (Cp) ligand, which is either unsubstituted or substituted, to form a first gas phase metal source;

A step c) of introducing the first gas phase metal source in the reaction chamber, in order to provoke their contact with said substrate, to generate the deposition of a metal containing dielectric film comprising a compound of the formula (I) as hereinbefore defined, on said substrate. Compound the formula $(II_1)$:

$$(R^2_tCp)M^1[N(R^{39})(R^{40})]_3 \qquad (II_1)$$

corresponding to the formula (II) as hereinabove defined in Claim 1, wherein $x=0$, $z=1$ and R' represents the group $N(R^{39})(R^{40})$.

22 Claims, 2 Drawing Sheets

METHOD OF FORMING DIELECTRIC FILMS, NEW PRECURSORS AND THEIR USE IN SEMICONDUCTOR MANUFACTURING

This application is a 371 of International PCT Application PCT/EP2007/052507, filed Mar. 16, 2007, which claims priority to PCT/EP06/062893 filed Jun. 2, 2006, the entire contents of which are incorporated herein by reference.

The invention relates to a method of forming high-k dielectric films such as hafnium or zirconium oxides or oxynitrides and their use for manufacturing semi-conductors.

With the shrink of the critical dimensions of the future generation of semi-conductor devices, the introduction of new materials, especially having high dielectric constant, is required. In CMOS architectures, high-k dielectrics are required to replace $SiO_2$ which reaches its physical limits, having typically a $SiO_2$ equivalent thickness of about 1 nm.

Similarly, high-k dielectrics are required in Metal-Insulator-Metal architectures for RAM applications. Various metal compositions have been considered to fulfill both the materials requirements (dielectric constant, leakage current, crystallization temperature, charge trapping) and the integration requirements (thermal stability at the interface, dry etching feasibility . . . ).

The Group IV based materials, such as $HfO_2$, $HfSiO_4$, $ZrO_2$, $ZrSiO_4$, $HfZrO_4$, $HfLnO_x$ (Ln being selected from the group comprising scandium, yttrium and rare-earth elements) and more generally HfMOx and ZrMOx, M being an element selected from Group II, Group IIIa and Group IIIb, or a transition metal, are among most promising materials. Furthermore, Group IV metals composition can also be considered for electrode and/or Cu diffusion barrier applications, such as TiN for mid-gap metal gate and HfN, ZrN, HfSi, ZrSi, HfSiN, ZrSiN, TiSiN for MIM electrodes.

The main industrial options to enable the deposition of such thin films with a reasonable throughput and an acceptable purity are vapor phase deposition techniques, such as MOCVD (Metal-organic Chemical Vapor Deposition) or ALD (Atomic Layer Deposition). Such deposition processes require metal precursors that must fulfill drastic requirements for a proper industrial use. Metal-organic or metal-halide precursors are required for those processes. Various hafnium and zirconium metal-organic compounds have been considered as precursors to enable such a deposition.

Halides such as $HfCl_4$, $ZrCl_4$ are the most common Hf/Zr precursors and have been widely described. Kim et al. disclosed the use of $HfCl_4$ for the deposition of $HfO_2$ by ALD (Kim et al., Electrochem Soc Proceedings 2005-05, 397, 2005). However, some by-products generated during the deposition process, such as HCl or $Cl_2$, can cause surface/interface roughness that can be detrimental to the final properties. Other possible byproducts, depending on the oxygen source used, may be hazardous. For instance, $OCl_2$, through the OCl fragment by QMS, has been detected as a byproduct of the reaction between $HfCl_4$ and $O_3$. Moreover, in the case of high-k oxide, Cl or F impurities are highly detrimental to the final electrical properties.

Triyoso et al. and Chang et al. studied the use of $Hf(OtBu)_4$ for $HfO_2$ MOCVD and ALD, respectively [Triyoso et al.; J. Electrochem. Soc., 152(3), G203-G209 (2005); Chang et al.; Electrochem. Solid. State Let., 7(6), F42-F44 (2004)]. Williams et al. have evaluated $Hf(mmp)_4$ and $Hf(OtBu)_2(mmp)_2$ for MOCVD of $HfO_2$. In WO2003035926, Jones et al. disclose solid Ti, Hf. Zr and La precursors improved with donor functionalized alkoxy ligand (1-methoxy-2-methyl-2-propanolate [$OCMe_2CH_2OMe$, mmp]) which helps inhibiting oligomerization of Zr and Hf alkoxide compounds and increasing their stability towards moisture. However, all those alkoxide precursors have the drawback not to enable self-limited deposition in ALD process as suggested by Potter et al. (R. J. Potter, P. R. Chalker, T. D. Manning, H. C. Aspinall, Y. F. Loo, A. C. Jones, L. M. Smith, G. W. Critchlow, M. Schumacher, Chem. Vap. Deposition, 2005, 11, N° 3, 159-167).

Alkylamides precursors such as $Hf(NEtMe)_4$, $Hf(NMe_2)_4$, $Hf(NEt_2)_4$ have been widely disclosed in the literature [Senzaki et al, J. Vac. Sci. Technol. A 22(4) July/August 2004; Haussmann et al, Chem. Mater. 2002, 14, 4350-4353; Kawahara et al., J. Appl. Phys., Vol 43, N° 7A, 2004, pp 4129-4134; Hideaki et al., JP 2002-093804; Metzner et al. U.S. Pat. No. 6,858,547; Dip et al. US 2005/0056219 A1]. Group IV alkylamides are both suitable for ALD and MOCVD processes. Furthermore, some are liquid at room temperature (Hf $(NEt_2)_4$ and $Hf(NEtMe)_4$) and of sufficient volatility, and they allow self-limited ALD at low temperature for a limited thermal budget process. However, Group IV alkylamides, alkylamides in particular Zr compounds, have several drawbacks, among which they may decompose during the distribution to some extent leading to a possible clogging of the feeding line or the vaporizer, they may generate particles during deposition, they may entail non-uniform compositions during deep trenches deposition processes, and they only allow a narrow self-limited ALD temperature window, hence reducing the process window. In particular, $Zr(NEtMe)_4$ may decompose in the distribution lines and generate particles above 170° C. which is a common distribution temperature. $Hf(NEtMe)_4$ is more thermally stable yet do not afford self-limited atomic layer deposition above 300° C. due to thermal decomposition.

In WO 2007/055088, Thenappan et al. disclose hafnium and zirconium guanidinates complexes and their application for vapor phase deposition. $Hf(NEt_2)_2[(NiPr—CNEt_2]_2$ is given as example. Hafnium and zirconium guanidinates are however generally solids with a very limited volatility. As exemplified in thermal gravimetric analysis, one may not obtain $Hf(NEt_2)_2[(NiPr—CNEt_2]_2$ in vapour phase, without a risk of thermal decomposition and a subsequent particle generation.

Lehn et al. (Chem. Vap. Deposition, 2006, 12, 280-284) disclose tetrakis(trimethylhydrazido) zirconium [$Zr(NMeNMe_2)_4$,] and hafnium and their use for low temperature CVD. The exemplified compounds have an acceptable volatility (sublimation at 0.06 Torr, 90° C. reported) but they are solid at room temperature.

Carta et al. disclose the use of bis(cyclopentadienyl)bisdimethyl hafnium, [$HfCp_2Me_2$] (Carta et al. discloses in Electrochem Soc Proceedings, 260, 2005-09, 2005) and several authors (Codato et al., Chem Vapor Deposition, 159, 5, 1995; Putkonen et al., J Mater Chem, 3141, 11, 2001; Niinisto et al., Langmuir, 7321, 21, 2005) proposed a new family of Zr and Hf compounds as alternatives to hafnium and zirconium alkylamides: Bis(cyclopentadienyl)bisdimethyl hafnium, bis (cyclopentadienyl)bisdimethyl zirconium, which allow an efficient ALD deposition process with an ALD window up to 400° C. and an achievement of films with less than 0.2% C in optimized conditions with $H_2O$ as co-reactant. However, $HfCp_2Me_2$ and $ZrCp_2Me_2$ both have the drawback of being solid products at room temperature ($HfCp_2Me_2$ melting point is 57.5° C.). This prevents IC makers to use those precursors in an industrial manner, that is using delocalized containers filling, and entail both facilitation and process issues.

In U.S. Pat. No. 6,743,473, Parkhe et al. disclose the use of $(Cp(R)_n)_xMH_{y-x}$, to make a metal and/or a metal nitride layer, where M is selected from tantalum, vanadium, niobium and hafnium, Cp is cyclopentadienyl, R is an organic group. Only examples of tantalum and niobium cyclopentadienyl compounds are disclosed. However, no liquid precursor or a precursor having a melting point lower than 50° C. is disclosed.

Liquid bis(cyclopentadienyl) derivatives have recently been proposed by Heys et al. in WO 2006/131751 A1. However, they still present the disadvantage of limited volatility and also present large steric hindrance that may limit the achieved growth rate.

Today, there is a need for providing liquid or low melting point (<50° C.) group IV precursor compounds, and in particular Hf and Zr compounds, that would allow simultaneously a proper distribution (physical state, thermal stability at distribution temperatures), a wide self-limited ALD window, and a deposition of pure films either by ALD or MOCVD.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

Figure 1:
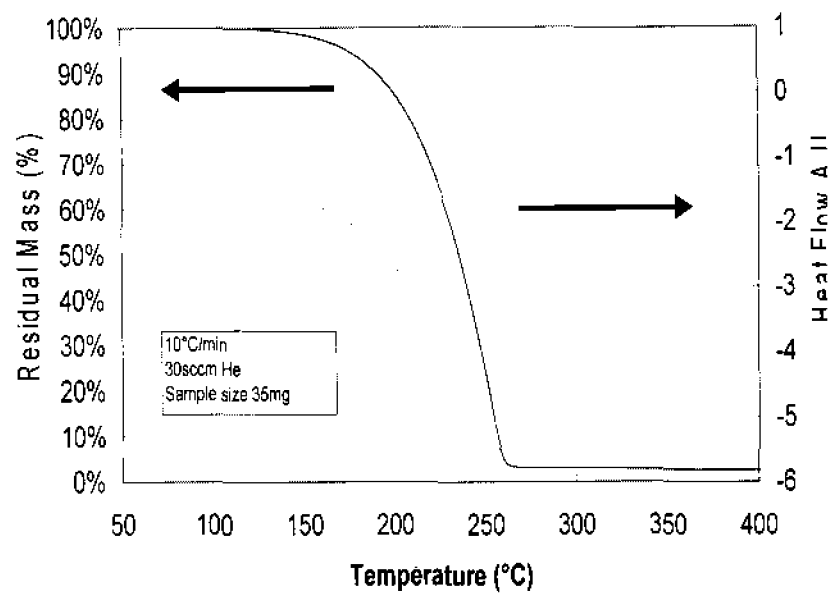
FIG. 1 is a thermal gravimetric analysis (TGA) graph illustrating the mass loss versus temperature results for $Zr(EtCp)(NMe_2)_3$.

According to the invention, certain cyclopentadienyl or pentadienyl based group IV metal-organic precursors have been found suitable for the deposition of Group IV metal containing thin films by either ALD or MOCVD processes and to have the following advantages:

They are liquid at room temperature or having a melting point lower than 50° C., They are thermally stable to enable proper distribution (gas phase or direct liquid injection) without particles generation, They are thermally stable to allow wide self-limited ALD window, 4) allowing deposition of a variety of Group IV metals containing films, including ternary or quaternary materials, by using one or a combination of co-reactants (selected from the group comprising of $H_2$, $NH_3$, $O_2$, $H_2O$, $O_3$, $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, TMA or an aluminum-containing precursor, TBTDET, TAT-DMAE, PET, TBTDEN, PEN, lanthanide-containing precursors such as $Ln(tmhd)_3$ ... ).

According to a first embodiment, the invention relates to a method of deposition on a substrate, of at least one metal containing dielectric film comprising a compound of the formula (I):

wherein:
0≤a≤1,
0≤b≤3, preferably 1.5≤b≤2.5;
0≤c≤1,
$M^1$ represents a metal selected from hafnium (Hf), zirconium (Zr) and titanium (Ti); and
$M^2$ represents a metal atom selected from magnesium (Mg), calcium (Ca), zinc (Zn), bore (B), aluminum (A), indium (In), silicon (Si), germanium (Ge), tin (Sn), hafnium (Hf), zirconium (Zr), titanium (Ti), vanadium (V), niobium (Nb), tantalum (Ta); and the Lanthanides atoms, more particularly scandium (Sc), yttrium (Y) and lanthanum (La) and rare-earth metal atoms, which comprises the following steps:

A step a) of providing a substrate into a reaction chamber;
A step (b) of vaporizing at least one $M^1$ metal containing precursor of the formula (II):

wherein:
$M^1$ is as hereinabove defined;
0≤x≤3, preferably x=0 or 1;
0≤z≤3, preferably z=1 or 2;
1≤(x+z)≤4;
0≤y≤7, preferably y=2 0≤t≤5, preferably t=1;
$(R^1_yOp)$ represents a pentadienyl (Op) ligand, which is either unsubstituted or substituted by one or more $R^1$ groups, y representing the number of substituting $R^1$ groups on said pentadienyl ligand;
$(R^2_tCp)$ represents a cyclopentadienyl (Cp) ligand, which is either unsubstituted or substituted by one or more $R^2$ groups, t representing the number of substituting $R^1$ groups on said cyclopentadienyl ligand;
$R^1$ and $R^2$, are identical or different and are independently selected from the group consisting of the chloro group, the linear or branched, alkyl groups having from one to four carbon atoms, the N-alkyl amino groups, wherein the alkyl group is linear or branched and has from one to four carbon atoms, the N,N-dialkyl amino groups, wherein each alkyl group, identical or different from the other, is linear or branched and has from one to four carbon atoms, the linear or branched alkoxy groups, having from one to four carbon atoms, the alkylsilylamides groups, the amidinates groups and the carbonyl group;
R' represents a ligand independently selected from the group consisting of the hydrogen, fluoro, chloro, bromo or iodo atoms, the linear or branched, alkyl groups having from one to four carbon atoms, the N-alkyl amino groups, wherein the alkyl group is linear or branched and has from one to four carbon atoms, the N,N-dialkyl amino groups, wherein each alkyl group, identical or different from the other, is linear or branched and has from one to four carbon atoms, the linear or branched alkoxy groups, having from one to four carbon atoms, the alkylsilyl amino groups wherein the alkyl group is linear or branched and has from one to four carbon atoms, the dialkylsilyl amino groups wherein each alkyl group, identical or different from the other, is linear or branched and has from one to four carbon atoms, the trialkylsilyl amino groups wherein each alkyl group, identical or different from the other, is linear or branched and has from one to four carbon atoms, the amidinates groups and the carbonyl, being understood that, if said formula (II) comprises more than one R' groups, each R' may be identical or different one from another,
to form a first gas phase metal source;
Optionally a step b') of vaporizing at least one $M^2$ metal containing precursor, $M^2$ being as hereinabove defined; to form an optional second gas phase metal source;
A step c) of introducing said first gas phase metal source and said optional second gas phase metal source, in the reaction chamber, in order to provoke their contact with said substrate, to generate the deposition of a metal containing dielectric film comprising a compound of the formula (I) as hereinbefore defined, on said substrate;

provided that, if the at least one metal containing dielectric film to be formed comprises the compound of the formula (I'):

$$M^1{}_1O_2 \quad (I'),$$

corresponding to the formula (I), as hereinbefore defined wherein, a=0, b=2, and c=0, and if the $M^1$ metal containing precursor, which is involved in step b), is a compound of the formula (II'):

$$(R^2{}_tCp)_2M^1R'_2 \quad (II'),$$

corresponding to the formula (II) as hereinabove defined wherein x=0, and z=2, in said formula (II'), t>0 in at least one of the two $(R^2{}_tCp)$ ligands.

In the method as hereinabove defined, the at least one metal containing precursor of the formula (II) and if necessary, the least one $M^2$ metal containing precursor, have a melting point generally below 50° C., preferably below 35° C. and they are preferably liquid at room temperature.

According to a particular embodiment of the method as hereinbefore defined, the vaporization step b) and if necessary, the vaporization step b') are achieved by introducing a carrier gas into a heated container containing the at least one $M^1$ metal containing precursor of the formula (II):

$$(R^1{}_yOp)_x(R^2{}_tCp)_zM^1R'_{4-x-z} \quad (II)$$

and if necessary, both the at least one $M^2$ metal containing precursor. The container is preferably heated at a temperature allowing to get the said metal sources in liquid phase and at a sufficient vapor pressure. If necessary, one or both metal precursors may be mixed to a solvent or to a mixture of solvents and/or to a stabilizer. The said solvent is for example selected from octane, hexane, pentane or tetramethylsilane. The concentration of the metal precursors in the solvant or in the mixture of solvents is usually between 0.01M and 0.5M and is more particularly around 0.05M. The carrier gas is selected, without limitation, from Ar, He, $H_2$, $N_2$ or mixtures of thereof. If necessary, the container may be heated at temperatures in the range of 80-110° C. Those skilled in the art will consider that the temperature of the container can be adjusted to control the amount of precursor to be vaporized.

The carrier gas flow is usually comprised between 10 sccm (standard cubic centimeter) and 500 sccm. Preferably, the carrier gas flow is comprised between 50 sccm and 200 sccm.

According to another particular embodiment of the method as hereinbefore defined, the vaporization step b) and if necessary, the vaporization step b') are achieved by introducing in a liquid form, the $M^1$ metal containing precursor of the formula (II):

$$(R^1{}_yOp)_x(R^2{}_tCp)_zM^1R'_{4-x-z} \quad (II)$$

and if necessary both the $M^2$ metal containing precursor to a vaporizer where it is vaporized. If necessary, one or both metal precursors may be mixed to a solvent or to a mixture of solvents and/or to a stabilizer. The said solvent is for example selected from octane, hexane, pentane or tetramethylsilane. The concentration of the metal precursors in the solvant or in the mixture of solvents is usually between 0.01M and 0.5M and is more particularly around 0.05M.

According to a more particular embodiment, the vaporization step b) and the vaporization step b') are combined in one vaporization step b") of both sources.

During the step c) of the method as hereinbefore defined, the vaporized metal containing precursor is introduced into a reaction chamber where it is contacted to a substrate.

In the context of the present invention, substrate means any substrate used in the semiconductors manufacturing, which, because of their technical function, requires to be coated by metal containing films. Such substrates are for example not only selected from silicon substrates (Si), silica substrates ($SiO_2$), silicon nitride substrates (SiN) or silicon oxy nitride substrates (SiON), but also from tungsten substrates (W) or noble metal substrates such as for example, Platinum substrates (Pt), Palladium substrates (Pd), Rhodium substrates (Rh) or gold substrates (Au).

The substrate is heated until the required temperature to obtain the desired film with a sufficient growth rate and with the desired physical state and composition.

The temperature during step c), usually ranges from 150° C. to 600° C. Preferably the temperature is lower or equal to 450° C.

The pressure in the reaction chamber is controlled to obtain the desired metal containing film with a sufficient growth rate. The pressure during step c) usually ranges from around 1 mTorr (0.1333224 Pa) to around 100 Torr (13332.24 Pa).

In the context of the present invention, the $M^2$ metal containing precursor, is selected from the group consisting of:

Silicon derivatives or their Germanium homologues, such as:

disiloxane, trisilylamine, disilane, trisilane, alkoxysilane of the formula: $(III_1)$ $$SiH_x(OR^3)_{4-x}, \quad (III_1)$$

wherein: $0 \leq x \leq 3$ and $R^3$ represents a linear or branched hydrocarbon group having 1 to 6 carbon atoms; silanol derivative of the formula $(III_2)$:

$$Si(OH)_x(OR^4)_{4-x} \quad (III_2)$$

wherein: $0 \leq x \leq 3$ and $R^4$ represents a linear or branched alkyl group, having 1 to 6 carbon atoms, preferably $Si(OH)(OR^4)_3$ and more preferably $Si(OH)(OtBu)_3$; aminosilane derivative of the formula $(III_3)$:

$$SiH_x(NR^5R^6)_{4-x} \quad (III_3)$$

wherein: $0 \leq x \leq 3$ and $R^5$ and $R^6$ are identical or different and independently represents an hydrogen atom or a linear or branched alkyl having 1 to 6 carbon atoms, preferably SiH$(NMe_2)_3$ (TriDMAS); $SiH_2(NHtBu)_2$ (BTBAS); $SiH_2(NEt_2)_2$ (BDEAS)) and mixtures thereof;

Aluminum derivatives, such as trimethylaluminum [Al$(CH_3)_3$], dimethyl aluminum hydride [AlH$(CH_3)_2$], alkoxyalane of the formula $(IV_1)$:

$$AlR^8{}_x(OR^7)_{3-x} \quad (IV_1)$$

wherein: $0 \leq x \leq 3$ and $R^7$ represents a linear or branched alkyl having 1 to 6 carbon atom, and $R^8$, identical to or different from $R^7$, represents an hydrogen atom, or preferably $AlR^9R^{10}(OR^7)$, with $R^9$ and $R^{10}$ identical or different, which independently represent an linear or branched alkyl having 1 to 6 carbon atoms, most preferably $AlMe_2(OiPr)$; amidoalane of the formula $(IV_2)$:

$$AlR^{11}{}_x(NR^{12}R^{13})_{3-x} \quad (IV_2)$$

wherein: $0 \leq x \leq 3$ and $R^{12}$ and $R^{13}$ identical or different, represent an hydrogen atom or a linear or branched alkyl having 1 to 6 carbon atoms, and $R^{11}$, identical to or different from $R^7$ and, represents an hydrogen atom or a linear or branched alkyl having 1 to 6 carbon atoms;

Tantalum derivatives, such as: $Ta(OMe)_5$, $Ta(OEt)_5$, $Ta(NMe_2)_5$, $Ta(NEt_2)_5$, $Ta(NEt_2)_5$, a tantalum derivative of the formula $(V_1)$:

$$Ta(OR^{14})_4[O-C(R^{15})(R^{16})-CH_2-OR^{17}]$$

wherein $R^{14}$, $R^{15}$, $R^{16}$ and $R^{17}$, identical or different, independently represent an hydrogen atom or a linear or branched alkyl having 1 to 6 carbon atoms, preferably Ta(OEt)$_4$(OCMe$_2$CH$_2$—OMe) (TAT-DMAE), a tantalum derivative of the formula (V$_2$):

$$Ta(OR^{18})_4[O—C(R^{19})(R^{20})—CH_2—N(R^{21})(R^{22})] \quad (V_2)$$

wherein R$^{18}$, R$^{19}$, R$^{20}$, R$^{21}$ and R$^{22}$ identical or different, independently represent an hydrogen atom or a linear or branched alkyl having 1 to 6 carbon atoms, a tatalum derivative of the formula (V$_3$):

$$Ta(=NR^{24})(NR^{25}R^{26})_3 \quad (V_3)$$

wherein R$^{24}$, R$^{25}$ and R$^{26}$, identical or different, independently represent an hydrogen atom or a linear or branched alkyl having 1 to 6 carbon atoms;

Niobium derivatives, such as Nb(OMe)$_5$, Nb(OEt)$_5$, Nb(NMe$_2$)$_5$, Nb(NEt$_2$)$_4$, Nb(NEt$_2$)$_5$, a niobium derivative of the formula (VI$_1$):

$$Nb(OR^{27})_4(O—C(R^{28})(R^{29})—CH_2—OR^{30}) \quad (VI_1)$$

wherein R$^{27}$, R$^{28}$, R$^{29}$ and R$^{30}$, identical or different, independently represent an hydrogen atom or a linear or branched alkyl having 1 to 6 carbon atoms, preferably Nb(OEt)$_4$(OCMe$_2$CH$_2$—OMe) (NBT-DMAE), a niobium derivative of the formula (VI$_2$):

$$Nb(OR^{31})_4[O—C(R^{32})(R^{33})—CH_2—N(R^{34})(R^{35})] \quad (VI_2)$$

wherein R$^{31}$, R$^{32}$, R$^{33}$, R$^{34}$ and R$^{35}$ identical or different, independently represent an hydrogen atom or a linear or branched alkyl having 1 to 6 carbon atoms, a niobium derivative of the formula (VI$_3$):

$$Nb(=NR^{36})(NR^{37}R^{38})_3 \quad (VI_3)$$

wherein R$^{36}$, R$^{37}$ and R$^{38}$, identical or different, independently represent an hydrogen atom or a linear or branched alkyl having 1 to 6 carbon atoms;

lanthanide derivatives, such as scandium derivatives, yttrium derivatives, cerium derivatives, praseodinum derivatives, gadolinium derivatives, dysprosium derivatives, erbium derivatives, lanthanum derivatives, a derivative with at least one β-diketonate ligand or at least a cyclopentadienyl ligand optionally substituted with one or several linear or branched alkyl groups having 1 to 6 carbon atoms;

divalent metal derivatives, such as strontium (Sr), barium (Ba), magnesium (Mg), calcium (Ca) or zinc (Zn) derivatives, with at least one β-diketonate ligand or at least a cyclopentadienyl ligand optionally substituted with one or several linear or branched alkyl groups having 1 to 6 carbon atoms;

other metal derivatives such as tungsten (W), molybdenum (Mo), hafnium (Hf) or zirconium (Zr) derivatives, for example the alkoxy derivatives, the amino derivatives or adducts containing these species, being understood that said derivatives are not compounds of the formula (II) as hereinbefore defined.

According to another particular embodiment, the method as hereinbefore defined, comprise:

A step d), wherein the at least one M$^1$ metal containing precursor of the formula (II), and if necessary, the at least one M$^2$ metal containing precursor, is mixed to at least one reactant specie prior to step c).

In the context of the invention, the at least one reactant specie is chosen in relation to the targeted metal based film, which is expected According to another embodiment, the reactant specie is an oxygen source and more particularly oxygen (O$_2$), oxygen containing radicals O. or OH., for instance generated by a remote plasma, ozone (O$_3$), moisture (H$_2$O) and H$_2$O$_2$ and mixture thereof.

According to another embodiment, the reactant specie is a nitrogen source and more particularly nitrogen (N$_2$), nitrogen-containing radicals such as N., NH., NH$_2$., ammonia (NH$_3$), hydrazine (NH$_2$NH$_2$) and its alkyl or aryl derivatives, and mixtures thereof.

According to another embodiment, the reactant specie is both a nitrogen and an oxygen source and more particularly, NO, NO$_2$, N$_2$O, N$_2$O$_5$, N$_2$O$_4$ and mixtures thereof.

Depending on the ratio N/O, which is required, the reactant specie which is, if necessary, used in the method as hereinbefore defined, may be either an oxygen source, either a mixture of an oxygen source and of a nitrogen source either both an oxygen and a nitrogen source or a mixture thereof.

According to another embodiment of the invention, if the targeted metal based film contains carbon, such as for example without limitation metal carbide or metal carbonitride, at least one reactant specie is a carbon source more particularly, methane, ethane, propane, butane, ethylene, propylene, t-butylene, According to another embodiment of the invention if the targeted metal based film contains silicon, such as for example without limitation metal silicide, silico-nitride, silicate or silico-carbo-nitride, at least on reactant specie is a silicon source such as:

disiloxane, trisilylamine, disilane (Si$_2$H$_6$), trisilane (Si$_3$H$_8$), alkoxysilane of the formulas (III$_1$), (III$_2$) or (III$_3$), as hereinbefore defined, for example SiH(NMe$_2$)$_3$ (TriDMAS); SiH$_2$(NHtBu)$_2$ (BTBAS); SiH$_2$(NEt$_2$)$_2$ (BDEAS)) and mixtures thereof.

According to another particular embodiment, the method as hereinbefore defined, comprise:

a step d') wherein the at least one M$^1$ metal containing precursor of the formula (II) and if necessary, the at least one M$^2$ metal containing precursor, is mixed to at least one reactant specie in the reaction chamber.

The mode of introduction of the at least one M$^1$ metal containing precursor of the formula (II) and if necessary, the at least one M$^2$ metal containing precursor, and the at least one reactant specie in the reaction chamber generally depends on the mode of deposition of the film on the substrate. The metal containing precursors and the reactant species are generally introduced simultaneously in a chemical vapor deposition process, or sequentially in an atomic layer deposition process or according to several combinations, as for example in a pulsed modified atomic layer deposition process wherein the at least one M$^1$ metal containing precursor of the formula (II) and if necessary, the at least one M$^2$ metal containing precursor, are introduced together in one pulse and the at least one reactant specie is introduced in a separate pulse; or in a pulsed chemical vapor deposition process wherein the at least one M$^1$ metal containing precursor of the formula (II) and if necessary, the at least one M$^2$ metal containing precursor, are introduced by pulse and the at least one reactant specie is introduced continuously.

According to another of the invention, the at least one reactant specie is passed through a plasma system localized remotely from the reaction chamber, and decomposed to radicals.

According to another embodiment, the step (b) of the method as hereinabove defined, consists of a step (b$_1$) of mixing at least one first metal containing precursor of the formula (II) together with at least a second of the following precursors: M$^1$(NMe$_2$)$_4$, M$^1$(NEt$_2$)$_4$, M$^1$(NMeEt)$_4$, M$^1$(mmp)$_4$, M$^1$(OtBu)$_4$, M$^1$(OtBu)$_2$(mmp)$_2$ and mixtures thereof and a step (b$_2$) of vaporizing said mixture.

According to a more particular embodiment, the invention concerns a method as hereinbefore defined, of deposition of a metal containing dielectric film comprising a compound of the formula (I), wherein the $M^1$ metal containing precursor is of the formula ($II_1$):

$$(R^2{}_xCp)M^1[N(R^{39})(R^{40})]_3 \quad (II_1)$$

corresponding to the formula (II), wherein x=0 z=1 and R' represents the group $N(R^{39})(R^{40})$, wherein $R^{39}$ and $R^{40}$, identical or different, independently represent an hydrogen atom, a linear or branched alkyl group having from one to four carbon atoms, an alkylsilyl group, wherein the alkyl group is linear or branched and has from one to four carbon atoms, a dialkylsilyl group, wherein each alkyl group, identical or different from the other, is linear or branched and has from one to four carbon atoms or a trialkylsilyl group wherein each alkyl group, identical or different from the other, is linear or branched and has from one to four carbon atoms According to a more particular embodiment, the invention concerns a method as hereinbefore defined, of deposition of a metal containing dielectric film comprising a compound of the formula ($I_1$):

$$M^1O_2 \quad (I_1)$$

corresponding to the formula (I), wherein a=0, b=2 and c=0 wherein the metal containing precursor of the formula (II) is selected from the group consisting of: $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixtures thereof.

According to a more particular embodiment, the invention concerns a method as hereinbefore defined, of deposition of a metal containing dielectric film comprising a compound of the formula ($I_2$):

$$M^1O_bN_c \quad (I_2)$$

corresponding to the formula (I), wherein a=0, 1.5≤b≤2.5 and 0<c≤0.5, wherein the metal containing precursor of the formula (II) is selected from the group consisting of: $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and mixture thereof.

According to a more particular embodiment, the invention concerns a method as hereinbefore defined, of deposition of a metal containing dielectric film comprising a compound of the formula ($I_3$):

$$(M^1{}_{1-a}M^2{}_a)O_b \quad (I_3)$$

corresponding to the formula (I), wherein 0≤a<1 and c=0, wherein the metal containing precursor of the formula (II) is selected from the group consisting of: $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$ and the $M^2$ metal containing precursor is preferably selected from the silicon derivatives or their germanium homologues, the tantalum derivatives, lanthanide derivatives, and the magnesium derivatives as hereinabove defined.

According to a more particular embodiment, the invention concerns a method as hereinbefore defined, of deposition of a metal containing dielectric film comprising a compound of the formula ($I_4$):

$$(M^1{}_{1-a}M^2{}_a)O_bN_c \quad (I_4)$$

corresponding to the formula (I), wherein 0≤a<1 and 0<c≤0.5, wherein the metal containing precursor of the formula (II) is selected from the group consisting of $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, $ZrCp(NEt_2)_3$, $Zr(iPr_2Cp)(NMe_2)_3$, $Zr(tBu_2Cp)(NMe_2)_3$, $Hf(MeCp)(NMe_2)_3$, $Hf(EtCp)(NMe_2)_3$, $HfCp(NMe_2)_3$, $Hf(MeCp)(NEtMe)_3$, $Hf(EtCp)(NEtMe)_3$, $HfCp(NEtMe)_3$, $Hf(MeCp)(NEt_2)_3$, $Hf(EtCp)(NEt_2)_3$, $HfCp(NEt_2)_3$, $Hf(iPr_2Cp)(NMe_2)_3$, $Hf(tBu_2Cp)(NMe_2)_3$, the $M^2$ metal containing precursor is preferably selected from the silicon derivatives or their germanium homologues, the tantalum derivatives, lanthanide derivatives, and the magnesium derivatives as hereabove defined, and at least one oxygen containing precursor and at least one nitrogen containing precursor is introduced into the reactor.

According to another embodiment the invention concerns the use of the compounds of the formula (II) as hereinbefore defined, to make dielectric films more particularly for integrated circuits or in the preparation of Metal Insulator Metal (MIM) architectures for Random Access Memories.

According to another embodiment, the invention concerns a compound the formula ($II_1$):

$$(R^2{}_xCP)M^1[N(R^{39})(R^{40})]_3 \quad (II_1)$$

corresponding to the formula (II), wherein x=0, z=1 and R' represents the group $N(R^{39})(R^{40})$, wherein $R^{39}$ and $R^{40}$, identical or different, independently represent an hydrogen atom, a linear or branched alkyl group having from one to four carbon atoms, an alkylsilyl group, wherein the alkyl group is linear or branched and has from one to four carbon atoms, a dialkylsilyl group, wherein each alkyl group, identical or different from the other, is linear or branched and has from one to four carbon atoms or a trialkylsilyl group wherein each alkyl group, identical or different from the other, is linear or branched and has from one to four carbon atoms.

According to a particular embodiment, the invention relates to a compound of the formula (II$_1$) as hereinbefore defined, wherein R$^2$, R$^{39}$ and R$^{40}$, identical or different, independently represent a radical selected from the methyl, ethyl, propyl, isopropyl, butyl, isobutyl, sec-butyl and tert-butyl groups, and more specifically the following compounds: Zr(MeCp)(NMe$_2$)$_3$, Zr(EtCp)(NMe$_2$)$_3$, ZrCp(NMe$_2$)$_3$, Zr(MeCp)(NEtMe)$_3$, Zr(EtCp)(NEtMe)$_3$, ZrCp(NEtMe)$_3$, Zr(MeCp)(NEt$_2$)$_3$, Zr(EtCp)(NEt$_2$)$_3$, ZrCp(NEt$_2$)$_3$, Zr(iPr$_2$Cp)(NMe$_2$)$_3$, Zr(tBu$_2$Cp)(NMe$_2$)$_3$, Hf(MeCp)(NMe$_2$)$_3$, Hf(EtCp)(NMe$_2$)$_3$, HfCp(NMe$_2$)$_3$, Hf(MeCp)(NEtMe)$_3$, Hf(EtCp)(NEtMe)$_3$, HfCp(NEtMe)$_3$, Hf(MeCp)(NEt$_2$)$_3$, Hf(EtCp)(NEt$_2$)$_3$, HfCp(NEt$_2$)$_3$, Hf(iPr$_2$Cp)(NMe$_2$)$_3$, Hf(tBu$_2$Cp)(NMe$_2$)$_3$.

According to a more specific embodiment, the invention relates to the following compounds:
Zr(EtCp)(NMe$_2$)$_3$, Zr(MeCp)(NMe$_2$)$_3$, ZrCp(NMe$_2$)$_3$, Hf(EtCp)(NMe$_2$)$_3$, Hf(MeCp)(NMe$_2$)$_3$ and HfCp(NMe$_2$)$_3$.

Those skilled in the art will recognize that the hereinabove metal-organic compounds could be used for any other applications than vapour phase deposition processes, such as catalysts or any other industrial process or application requiring the use of metal-organic compounds . . . .

According to another embodiment, the invention concerns a process for the preparation of a compound of the formula (II$_1$) as hereinabove defined, which comprises:

a step 1, consisting of the preparation of the compound of the formula (VII$_1$):

wherein M$^1$, R$^2$ and t are as hereinabove defined for the formula (II), by the reaction of M$^1$Cl$_4$ with (R$^2_t$Cp)Na;

a step 2, consisting of the reaction of the compound of the formula (VII$_1$) prepared in step 1, with NH(R$^{39}$)(R$^{40}$), to produce the compound of the formula (II$_1$).

According to a last embodiment, the invention concerns the following compounds of the formula (II) as hereinabove defined:
Hf(EtCp)$_2$Me$_2$, Zr(MeCp)$_2$Me$_2$ or Zr(EtCp)$_2$Me$_2$.

The following examples are an illustration of the various embodiments of the present invention, without being a limitation.

Example I

Deposition of Metal Oxide Film M$^1$O$_2$ with M$^1$ Being Preferably Hafnium and Zirconium The film to be deposited comprises a compound of the formula (I) wherein a=0, b=2 and c=0.

To make the deposition of such film on the surface of a wafer or in a deep trench to manufacture MIM structures for DRAM, one need to vaporize the M$^1$ metal source as defined in step (b) and to introduce it into the reactor (preferably Hafnium or Zirconium), to inject an oxygen source, preferably moisture, oxygen or ozone into said reactor, react the products at appropriate temperature (preferably between 150° C. and 350° C.) and pressure (preferably between 25 Pa and 1000 Pa) for the duration necessary to achieve either a thin film deposition on the substrate or to fill out deep trenches by ALD or pulse CVD process (sequential pulse injection of metal sources are necessary in order to allow regular deposition of the oxide in the trench to progressively fill out this trench and provide no voids in the dielectric film and therefore no defect in the capacitor dielectric film).

The dielectric film shall have the desired final composition (here essentially variations of the b value around 2 modifying the ratio of precursor to oxygen source).

Three examples of types of compounds of the formula (II) were chosen according to the three following options a, b or c:

a) The compound of the formula (II) is chosen from Zr(MeCp)$_2$Me$_2$, Zr(EtCp)$_2$Me$_2$, Hf(MeCp)$_2$Me$_2$ and Hf(MeCp)$_2$Me$_2$.

Delivery of molecules in liquid form is usually carried out by bubbling an inert gas (N$_2$, He, Ar, . . . ) into the liquid and providing the inert gas plus liquid gas mixture to the reactor.

b) The compound of the formula (II) is chosen from Zr(2,4-Me$_2$Op)$_2$Me$_2$ and Hf(2,4-Me$_2$Op)$_2$Me$_2$.

c) The compound of the formula (II) is chosen from Zr(MeCp)(2,4-Me$_2$Op)Me$_2$ and Hf(MeCp)(2,4-Me$_2$Op)Me$_2$.

The oxygen source shall be preferably, without limitations, oxygen (O$_2$), oxygen radicals (for instance O. or OH.), such as radicals generated by a remote plasma system, ozone, NO, N$_2$O, NO$_2$, moisture (H$_2$O) and H$_2$O$_2$.

Regarding the deposition process by itself, the reactants can be introduced into the reactor simultaneously (chemical vapor deposition), sequentially (atomic layer deposition) or different combinations (one example is to introduce metal source and the other metal source together in one pulse and oxygen in a separate pulse [modified atomic layer deposition]; another option is to introduce oxygen continuously and/or to introduce the metal source by pulse (pulsed-chemical vapor deposition).

Example II

Deposition of Metal Oxynitride Films M$^1$ON with M$^1$ Being Preferably Hafnium and Zirconium The film to be deposited comprises a compound of the formula (I) wherein a=0 and b and c are different from zero.

All the information given in Example I, is applicable in this Example II, except that nitrogen needs to be introduced into the reactor.

The nitrogen shall be selected from a nitrogen source selected from the group comprising nitrogen (N$_2$), ammonia, hydrazine and alkyl derivatives, N-containing radicals (for instance N., NH., NH$_2$.), NO, N$_2$O, NO$_2$ or the like.

Example III

Deposition of M$^1$M$^2$ Metal Oxide Films with M$^1$ being Preferably Hf or Zr and M$^2$ Being Preferably Si or Al The film to be deposited comprises a compound of the formula (I) wherein a≠0, b≠0 and c=0.

All the information given in Example I, is applicable in this Example III, except that a M$^2$ metal source is additionally needed.

The M$^2$ containing precursor is also introduced into the reactor to crate the M$^2$ source of metal. This M$^2$ containing precursor source shall be preferably:

a) a silicon (or germanium) source, for example Si(OH)(OtBu)$_3$, SiH(NMe$_2$)$_3$ (TriDMAS); SiH$_2$(NHtBu)$_2$ (BTBAS) and SiH$_2$(NEt$_2$)$_2$ (BDEAS)

b) an aluminum source, for example AlMe$_2$(OiPr); or c) a tantalum (or niobium) source, for example Ta(OMe)$_5$, Ta(OEt)$_5$ and Ta(OEt)(OCMe$_2$CH$_2$—OMe) (TATDMAE);

The invention is directed to the deposition of dielectric films of the formula I, onto a support such as a wafer, in a reactor using ALD, CVD, MOCVD, pulse CVD processes.

Example IV

Deposition of $M^1M^2$ Metal Oxynitride Films with $M^1$ being Preferably Hf or Zr and $M^2$ being Preferably Si or Al The film to be deposited comprises a compound of the formula (I) wherein a≠0, b≠0 and c≠0.

All the information given in Example III, is applicable in this case, except that nitrogen needs to be introduced into the reactor.

The nitrogen source shall be selected from the group comprising nitrogen (N2), ammonia, hydrazine and alkyl derivatives, N-containing radicals (for instance N. NH., $NH_2$.), NO, $N_2O$, $NO_2$.

Example V

Synthesis of (ethylcyclopentadienyl)tris(dimethylamino)zirconium, $Zr(EtCp)(NMe_2)_3$ $Zr(EtCp)(NMe_2)_3$ is prepared in 3 steps.

The first step is the preparation of $Zr(EtCp)Cl_3$ by the reaction of (EtCp)Na over $ZrCl_4$;

The second step is the reaction $LiNMe_2$ with $Zr(EtCp)Cl_3$ to produce $Zr(EtCp)(NMe_2)_3$. The resulting compound is purified by distillation. Overall yield was 35%.

(Ethylcyclopentadienyl)tris(dimethylamino)zirconium has been found to be a stable liquid pale yellow compound.

TGA Analysis of $Zr(EtCp)(NMe_2)_3$

The thermal gravimetric apparatus was stored in an argon glove box with moisture and oxygen content maintained below 1 ppmv. Thermal gravimetric analysis was performed by placing a 35 mg sample in an aluminum crucible. The sample was then heated at a 10° C./min temperature ramp from 35° C. to 400° C. The mass loss was monitored as a function of the crucible temperature. The residue level was 2.6% with full evaporation temperatures of 260° C. The resulting graph is on FIG. 1.

Example VI

Atomic Layer Deposition of $ZrO_2$ Thin Films Using $Zr(EtCp)(NMe_2)_3$ $Zr(EtCp)(NMe_2)_3$ is stored into a container. The container is heated at 90° C. and $N_2$ is used as carrier gas at a flow of 50 sccm. The pressure the container is controlled at 50 Torr. $O_3$ is used as oxygen source. The substrate is heated at 350° C. During a first step, $Zr(EtCp)(NMe_2)_3$ is introduced into the reaction chamber during 2 s. A $N_2$ purge of 5 s is performed afterwards as second step. As third step, a pulse of $O_3$ is then introduced into the reaction chamber during 2 s, followed by a 2 s $N_2$ purge as fourth step. All four steps are repeated 100 times to obtain a $ZrO_2$ film. Self-limited atomic layer deposition is obtained.

Similar experiments can be performed with Hf analogs. Similar experiments can be conducted with $H_2O$ as oxygen source.

Example VII

Metal-Organic Chemical Vapor Deposition of $ZrO_2$ Using $Zr(EtCp)(NMe_2)_3$ $Zr(EtCp)(NMe_2)_3$ is stored into a container. The container is heated at 90° C. and $N_2$ is used as carrier gas at a flow of 50 sccm. The pressure in the container is controlled at 50 Torr. $Zr(EtCp)(NMe_2)_3$ is mixed to an $O_2/N_2$ gas mixture into the reaction chamber. The substrate is heated at 500° C. The pressure inside the reaction chamber is set at 10 Torr. A film of zirconium oxide is obtained.

Similar experiments can be performed with Hf analogs.

Example VIII

Comparison of $Zr(EtCp)(NMe_2)_3$ and $Zr(NEtMe)_4$ Thermal Behavior

Figure 2:
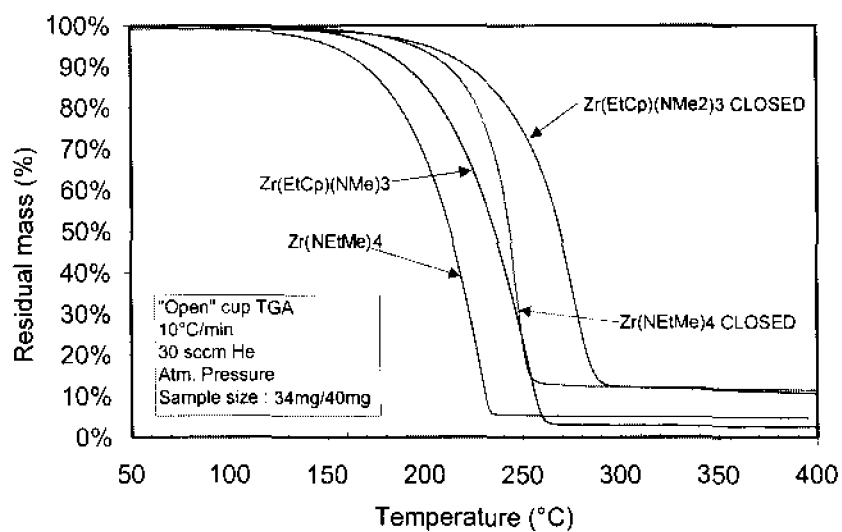
FIG. 2 is a TGA graph comparing the mass loss versus temperature results for $Zr(EtCp)(NMe_2)_3$ to that of $Zr(NEtMe)_4$.

Thermal gravimetric analysis is performed on $Zr(EtCp)(NMe_2)_3$ and $Zr(NEtMe)_4$ in similar conditions. Thermal gravimetric apparatus was stored in an argon glove box with moisture and oxygen content maintained below 1 ppmv. Thermal gravimetric analysis was performed by placing a 35 mg sample in an aluminum crucible. The sample was then heated at a 10° C./min temperature ramp from 35° C. to 400° C. The mass loss was monitored as a function of the crucible temperature. In closed cup configuration, a pierced pan (0.8 mm) is placed over the crucible containing the metal-organic compound to slow down the evaporation. This indicates the thermal stability at higher temperature. The results indicates that $Zr(EtCp)(NMe_2)_3$ is much more thermally stable than $Zr(NEtMe)_4$, making it further attractive for use as vapor phase precursor. The results are shown on FIG. 2.

Example IX

Synthesis and Thermal Behavior of $Hf(EtCp)_2Me_2$ $Hf(EtCp)_2Cl_2$ is readily obtained by the reaction of 1 mole $HfCl_4$ over EtCpNa.

Figure 3:
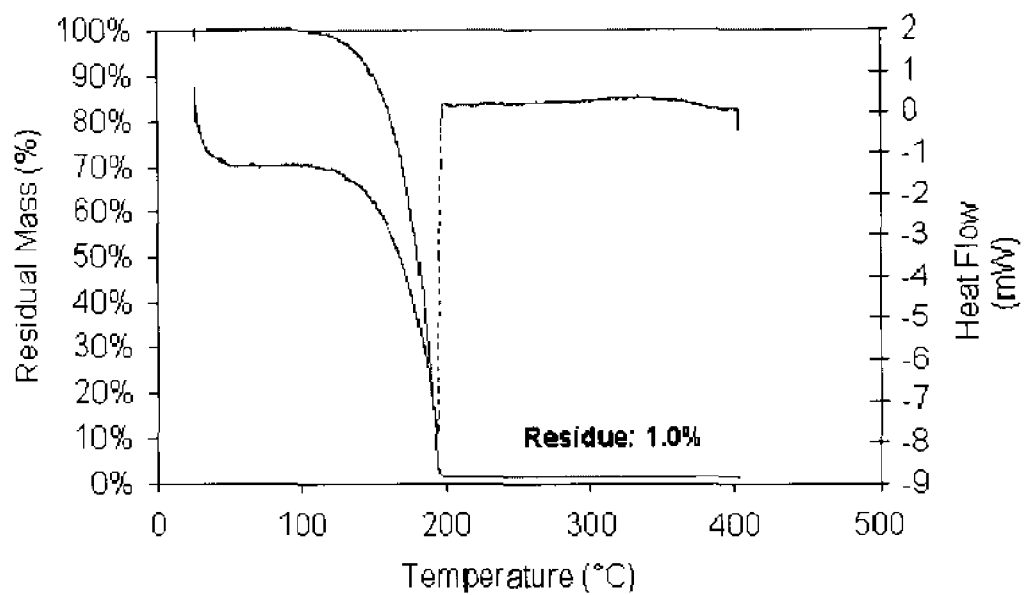
FIG. 3 is a TGA graph illustrating the mass loss versus temperature results for $Hf(EtCp)_2Me_2$.

$Hf(EtCp)_2Me_2$ is then obtained by a slow addition of 2 moles LiMe over 1 mole $Hf(EtCp)_2Cl_2$ at −20° C. and increasing the temperature until 0° C. The obtained transparent liquid $Hf(EtCp)_2Me_2$ is separated from LiCl and solvent by distillation. TGA analysis of $Hf(EtCp)_2Me_2$ in vacuum conditions, leaves a residue of 1.0% for a starting mass of about 30 mg. (see FIG. 3)

Example X

Atomic Layer Deposition of $HfO_2$ from $Hf(EtCp)_2Me_2$ and $O_3$

This example concerns the fabrication of hafnium oxide films. A silicon wafer is mounted in a deposition chamber that is provided with a heater over its circumference and the desired film is formed on the surface of the silicon wafer. The chamber is evacuated by a pump. The metal precursor, in this case dimethylhafnocene $HfMe_2(EtCp)_2$, is stored in a heated liquid container. Nitrogen gas is used as the carrier gas for the $Hf(EtCp)_2Me_2$. The $Hf(EtCp)_2Me_2$ in the liquid container is transported by flowing the nitrogen through the liquefied material. Nitrogen is transported through a mass flow controller into the vaporizer. The $Hf(EtCp)_2Me_2$ vapors were carried by nitrogen and fed to the chamber along, or diverted to a bypass line when the valve allowing the introduction of the precursor into the reactor is closed. An oxygen/ozone gas mixture (oxidizing agent) is also fed through a mass flow controller either into the chamber or to a bypass line. Oxygen/ozone on one side and Hf(EtCp)$_2$Me$_2$ on the other side were never introduced together to avoid a highly probable CVD reaction. They were usually introduced one by one, each reactant pulse being separated by purge time where only N$_2$ was introduced into the chamber.

Hafnium oxide films were produced at a ~0.7 A/cycle under the following conditions using the described tool: Pressure=3 torr, temperature=350° C., Hf(EtCp)$_2$Me$_2$ flow rate=0.5 sccm, O$_2$ flow rate=100 sccm. O$_3$ flow rate=8 sccm.N$_2$ flow rate=100 sccm.

Figure 4:
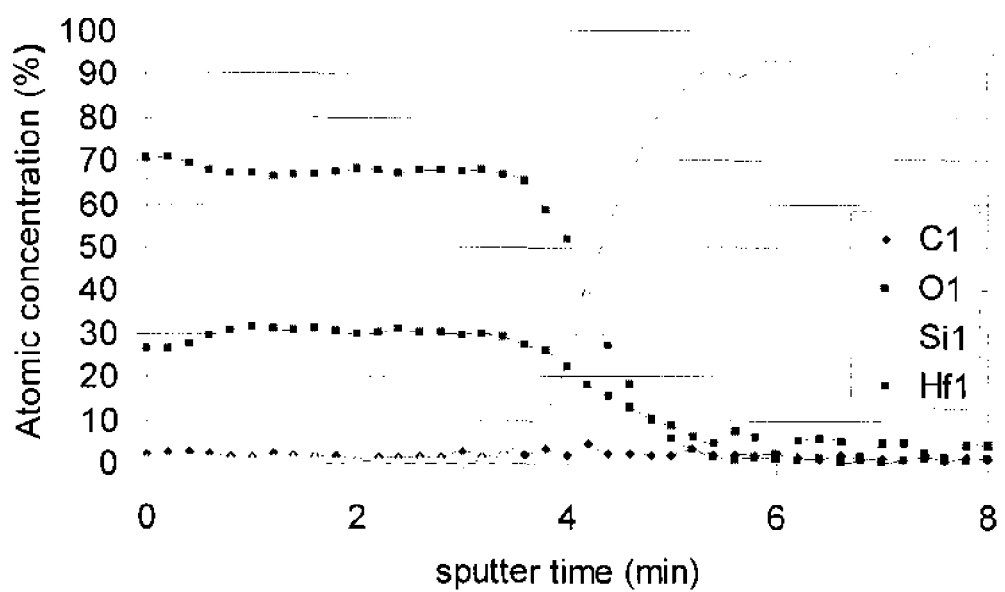
FIG. 4 is an Auger profile of the hafnium oxide film formed by $Hf(EtCp)_2Me_2$ and $O_3$.

An Auger profile of the obtained film is given as example (See FIG. 4).

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of deposition on a substrate, of at least one metal containing dielectric film comprising a compound of the formula (I):

$$(M^1{}_{1-a}M^2{}_a)O_bN_c, \quad (I)$$

wherein:
0≤a<1,
0<b≥3;
0≤c≤1,
M$^1$ is zirconium (Zr); and
M$^2$ represents a metal atom selected from magnesium (Mg), calcium (Ca), zinc (Zn), boron (B), aluminum (Al), indium (In), silicon (Si), germanium (Ge), tin (Sn), hafnium (Hf), zirconium (Zr), titanium (Ti), vanadium (V), niobium (Nb), tantalum (Ta); and the Lanthanides atoms and rare-earth metal atoms,
which comprises the following steps:
a step a) of providing a substrate into a reaction chamber;
a step b) of vaporizing at least one M$^1$ metal containing precursor to form a first gas phase metal source, the at least one M$^1$ metal containing precursor is selected from the group consisting of Zr(MeCp)(NMe$_2$)$_3$, Zr(EtCp)(NMe$_2$)$_3$, ZrCp(NMe$_2$)$_3$, Zr(MeCp)(NEtMe)$_3$, Zr(EtCp)(NEtMe)$_3$, ZrCp(NEtMe)$_3$, Zr(MeCp)(NEt$_2$)$_3$, Zr(EtCp)(NEt$_2$)$_3$, ZrCp(NEt$_2$)$_3$, Zr(iPr$_2$Cp)(NMe$_2$)$_3$, and Zr(tBu$_2$Cp)(NMe$_2$)$_3$;
optionally a step b') of vaporizing at least one M$^2$ metal containing precursor, M$^2$ being as hereinabove defined, to form an optional second gas phase metal source;
a step c) of introducing said first gas phase metal source and said optional second gas phase metal source, in the reaction chamber, in order to provoke their contact with said substrate, to generate the deposition of a metal containing dielectric film comprising a compound of the formula (I) as hereinbefore defined, on said substrate.

2. The method of claim 1, wherein the vaporization step b) and the vaporization step b') are combined in one vaporization step b") of both sources.

3. The method of claim 1, wherein the M$^2$ metal containing precursor, is selected from the group consisting of:
silicon derivatives or their germanium homologues;
silanol derivative of the formula (III$_2$):

$$Si(OH)_x(OR^4)_{4-x} \quad (III_2)$$

wherein: 1≤x≤3 and R$^4$ represents a linear or branched alkyl group, having 1 to 6 carbon atoms;
aminosilane derivative of the formula (III$_3$):

$$SiH_x(NR^5R^6)_{4-x} \quad (III_3)$$

wherein; 0≤x≤3 and R$^5$ and R$^6$ are identical or different and independently represents an hydrogen atom or a linear or branched alkyl having 1 to 6 carbon atoms;
aluminum derivatives;
amidoalane of the formula (IV$_2$):

$$AlR^{11}(NR^{12}R^{13})_{3-x} \quad (IV_2)$$

wherein: 0≤x≤3 and R$^{12}$ and R$^{13}$ identical or different, represent an hydrogen atom or a linear or branched alkyl having 1 to 6 carbon atoms, and R$^{11}$, identical to or different from R$^7$ and, represents an hydrogen atom or a linear or branched alkyl having 1 to 6 carbon atoms;
tantalum derivatives;
Niobium derivatives;
lanthanide derivatives;
divalent metal derivatives;
and other metal derivatives.

4. The method of claim 3, wherein the metal containing dielectric film comprises a compound of the formula (I$_3$):

$$(M^1{}_{1-a}M^2{}_a)O_b \quad (I_3)$$

corresponding to the formula (I), wherein 0≤a<1 and c=0, wherein the M$^2$ metal containing precursor is selected from the silicon derivatives or their germanium homologues, the tantalum derivatives, lanthanide derivatives, or the magnesium derivatives as hereabove defined.

5. The method of claim 3, wherein the metal containing dielectric film comprises a compound of the formula (I$_4$):

$$(M^1{}_{1-a}M^2{}_a)O_bN_c \quad (I_4)$$

corresponding to the formula (I), wherein 0≤a<1 and 0<c≤0.5, wherein the M$^2$ metal containing precursor is selected from the silicon derivatives or their germanium homologues, the tantalum derivatives, lanthanide derivatives, or the magnesium derivatives as hereabove defined, and at least one oxygen containing precursor and at least one nitrogen containing precursor is introduced into the reactor.

6. The method of claim 3, wherein the silicon derivatives or their germanium homologues are selected from the group consisting of disiloxane, digermoxane, trisilylamine, trigermylamine, disilane, digermane, trisilane, trigermane, alkoxysilane having the formula Si H$_x$(OR$^3$)$_{4-x}$, and alkoxygermane having the formula Ge H$_x$(OR$^3$)$_{4-x}$, wherein: 0≤x≤3 and R$^3$ represents a linear or branched hydrocarbon group having 1 to 6 carbon atoms.

7. The method of claim 3, wherein the silanol derivative is Si(OH)(OtBu)$_3$.

8. The method of claim 3, wherein the aminosilane derivative is selected from the group consisting of tris(dimethylamino)silane [SiH(NMe$_2$)$_3$], bis(tertbutylamino)silane [SiH$_2$(NHtBu)$_2$], bis(diethylamino)silane [SiH$_2$(NEt$_2$)$_2$], and mixtures thereof.

9. The method of claim 3, wherein the aluminum derivative is selected from the group consisting of trimethylaluminum [Al(CH$_3$)$_3$], dimethyl aluminum hydride [AlH(CH$_3$)$_2$], and alkoxyalane having the formula AlR$^8{}_x$(OR$^7$)$_{3-x}$, wherein 0≤x≤3, R$^7$ represents a linear or branched alkyl group having 1 to 6 carbon atoms, and R$^8$, identical to or different from R$^7$, represents a hydrogen atom or a linear or branched alkyl group having 1 to 6 carbon atoms.

10. The method of claim 9, wherein the aluminum derivative is $AlMe_2(OiPr)$.

11. The method of claim 3, wherein the tantalum derivative is selected from the group consisting of $Ta(OMe)_5$; $Ta(OEt)_5$; $Ta(NMe_2)_5$; $Ta(NEt_2)_5$; a tantalum derivative having the formula $Ta(OR^{14})_4[O-C(R^{15})(R^{16})-CH_2-OR^{17}]$, wherein $R^{14}$, $R^{15}$, $R^{16}$ and $R^{17}$, identical or different, independently represent a hydrogen atom or a linear or branched alkyl having 1 to 6 carbon atoms; a tantalum derivative having the formula $Ta(OR^{18})_4[O-C(R^{19})(R^{20})-CH_2-N(R^{21})(R^{22})]$, wherein $R^{18}$, $R^{19}$, $R^{21}$ and $R^{22}$, identical or different, independently represent a hydrogen atom or a linear or branched alkyl having 1 to 6 carbon atoms; and a tantalum derivative having the formula $Ta(=NR^{24})(NR^{25}R^{26})_3$, wherein $R^{24}$, $R^{25}$ and $R^{26}$, identical or different, independently represent an hydrogen atom or a linear or branched alkyl having 1 to 6 carbon atoms.

12. The method of claim 11, wherein the tantalum derivative is $Ta(OEt)_4(OCMe_2CH_2-OMe)$.

13. The method of claim 3, wherein the niobium derivative is selected from the group consisting of $Nb(OMe)_5$; $Nb(OEt)_5$; $Nb(NMe_2)_5$; $Nb(NEt_2)_4$; $Nb(NEt_2)_5$; a niobium derivative having the formula $Nb(OR^{27})_4(O-C(R^{28})(R^{29})-CH_2-OR^{30})$, wherein $R^{27}$, $R^{28}$, $R^{29}$ and $R^{30}$, identical or different, independently represent a hydrogen atom or a linear or branched alkyl having 1 to 6 carbon atoms; a niobium derivative having the formula $Nb(OR^{31})_4[O-C(R^{32})(R^{33})-CH_2-N(R^{34})(R^{35})]$, wherein $R^{31}$, $R^{32}$, $R^{33}$, $R^{34}$ and $R^{35}$, identical or different, independently represent a hydrogen atom or a linear or branched alkyl having 1 to 6 carbon atoms; and a niobium derivative having the formula $Nb(=NR^{36})(NR^{37}R^{38})_3$, wherein $R^{36}$, $R^{37}$ and $R^{38}$, identical or different, independently represent an hydrogen atom or a linear or branched alkyl having 1 to 6 carbon atoms.

14. The method of claim 13, wherein the niobium derivative is $Nb(OEt)_4(OCMe_2CH_2-OMe)$.

15. The method of claim 3, wherein the $M^2$ metal containing precursor is a hafnium derivative.

16. The method of claim 1, which further comprises:
A step d), wherein the at least one $M^1$ metal containing precursor and optionally the at least one $M^2$ metal containing precursor, is mixed to at least one reactant species prior to step c).

17. The method of claim 1, which further comprises:
a step d') wherein the at least one $M^1$ metal containing precursor and optionally the at least one $M^2$ metal containing precursor, is mixed to at least one reactant species in the reaction chamber.

18. The method of claim 1, wherein the metal containing dielectric film comprises a compound of the formula $(I_1)$:

$$M^1O_2 \qquad (I_1)$$

corresponding to the formula (I), wherein a=0, b=2 and c=0.

19. The method of claim 1, wherein the metal containing dielectric film comprises a compound of the formula $(I_2)$:

$$M^1O_bN_c \qquad (I_2)$$

corresponding to the formula (I), wherein a=0, 1.5≤b≤2.5 and 0<c≤0.5.

20. The method of claim 1, wherein the at least one $M^1$ metal containing precursor is $ZrCp(NMe_2)_3$.

21. The method of claim 1, wherein the at least one $M^1$ metal containing precursor is $Zr(MeCp)(NMe_2)_3$.

22. The method of claim 1, wherein the at least one M metal containing precursor is $Zr(EtCp)(NMe_2)_3$.

* * * * *

(12) EX PARTE REEXAMINATION CERTIFICATE (10772nd)
United States Patent
Dussarrat et al.

(10) Number: US 8,668,957 C1
(45) Certificate Issued: *Dec. 7, 2015

(54) METHOD OF FORMING DIELECTRIC FILMS, NEW PRECURSORS AND THEIR USE IN SEMICONDUCTOR MANUFACTURING

(75) Inventors: Christian Dussarrat, Tokyo (JP); Nicolas Blasco, Grenoble (FR); Audrey Pinchart, Toulouse (FR); Christophe Lachaud, Saint Michel sur Orge (FR)

(73) Assignee: L'AIR LIQUIDE, SOCIETE ANONYME POUR L'ETUDE ET L'EXPLOITATION DES PROCEDES GEORGES CLAUDE, Paris (FR)

Reexamination Request:
No. 90/013,316, Aug. 6, 2014

Reexamination Certificate for:
Patent No.: 8,668,957
Issued: Mar. 11, 2014
Appl. No.: 12/303,169
PCT Filed: Mar. 16, 2007
PCT No.: PCT/EP2007/052507
§ 371 (c)(1),
(2), (4) Date: Apr. 3, 2009
PCT Pub. No.: WO2007/141059
PCT Pub. Date: Dec. 13, 2007

( * ) Notice: This patent is subject to a terminal disclaimer.

(30) Foreign Application Priority Data

Jun. 2, 2006 (WO) ............... PCT/EP2006/062893

(51) Int. Cl.
| | |
|---|---|
| *C23C 16/40* | (2006.01) |
| *C23C 16/34* | (2006.01) |
| *C23C 16/30* | (2006.01) |
| *C07F 17/00* | (2006.01) |
| *H01L 21/316* | (2006.01) |
| *C07F 7/00* | (2006.01) |
| *C23C 16/18* | (2006.01) |
| *H01L 21/314* | (2006.01) |

(52) U.S. Cl.
CPC . *C23C 16/34* (2013.01); *C07F 7/00* (2013.01); *C07F 7/006* (2013.01); *C07F 17/00* (2013.01); *C23C 16/18* (2013.01); *C23C 16/308* (2013.01); *C23C 16/405* (2013.01); *H01L 21/3141* (2013.01); *H01L 21/31641* (2013.01); *H01L 21/31645* (2013.01)

(58) Field of Classification Search
None
See application file for complete search history.

(56) References Cited

To view the complete listing of prior art documents cited during the proceeding for Reexamination Control Number 90/013,316, please refer to the USPTO's public Patent Application Information Retrieval (PAIR) system under the Display References tab.

*Primary Examiner* — Ling Xu

(57) ABSTRACT

Method of deposition on a substrate, of a metal containing dielectric film comprising a compound of the formula (I):

$$(M^1_{1-a}M^2_a)O_bN_c, \quad (I)$$

wherein $0 \le a < 1$, $0 < b \le 3$, $0 \le c \le 1$, $M^1$ represents a metal selected from (Hf), (Zr) and (Ti); and $M^2$ represents a metal atom atoms, which comprises the following steps:

A step a) of providing a substrate into a reaction chamber;
A step (b) of vaporizing a $M^1$ metal containing precursor of the formula (II):

$$(R^1_y Op)_x (R^2_t Cp)_z M^1 R'_{4-x-z} \quad (II)$$

wherein $0 \le x \le 3$, preferably $x=0$ or 1, $0 \le z \le 3$, preferably $z=1$ or 2, $1 \le (x+z) \le 4$, $0 \le y \le 7$, preferably $y=2$ $0 \le t \le 5$, preferably $t=1$, $(R^1_y Op)$ represents a pentadienyl ligand, which is either unsubstituted or substituted; $(R^2_t Cp)$ represents a cyclopentadienyl (Cp) ligand, which is either unsubstituted or substituted, to form a first gas phase metal source;

A step c) of introducing the first gas phase metal source in the reaction chamber, in order to provoke their contact with said substrate, to generate the deposition of a metal containing dielectric film comprising a compound of the formula (I) as hereinbefore defined, on said substrate. Compound the formula (II₁):

$$(R^2_t Cp)M^1[N(R^{39})(R^{40})]_3 \quad (II_1)$$

corresponding to the formula (II) as hereinabove defined in Claim 1, wherein $z=0$, $z=1$ and R' represents the group $N(R^{39})(R^{40})$.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 11-12 are cancelled.

Claims 1, 3-6 and 15-22 are determined to be patentable as amended.

Claims 2, 7-10 and 13-14, dependent on an amended claim, are determined to be patentable.

New claims 23-35 are added and determined to be patentable.

1. A method of deposition on a substrate[,] of at least one [metal containing] dielectric film comprising a compound of the formula (I):

$$(M^1_{1-a}M^2_a)O_bN_c,  \quad (I)$$

wherein:
0≤a<1,
0≤b[≥]>3;
0≤c≤1,
$M^1$ is zirconium (Zr); and
$M^2$ represents [a metal] *an* atom selected from magnesium (Mg), calcium (Ca), zinc (Zn), boron (B), aluminum (Al), indium (In), silicon (Si), germanium (Ge), tin (Sn), hafnium (Hf), zirconium (Zr), titanium (Ti), vanadium (V), niobium (Nb), tantalum (Ta)[; and], the Lanthanides atoms [and], *or* rare-earth [metal] atoms, which comprises the following steps:

a step a) of providing a substrate into a reaction chamber;

a step b) of vaporizing at least one *liquid* $M^1$ [metal] containing precursor to form a first gas phase [metal] $M^1$ source, the at least one *liquid* $M^1$ [metal] containing precursor [is] selected from the group consisting of $Zr(MeCp)(NMe_2)_3$, $Zr(EtCp)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)(NEt_2)_3$, $Zr(EtCp)(NEt_2)_3$, *and* $ZrCp(NEt_2)_3$[, $Zr(iPr_2Cp)(NMe_2)_3$, and $Zr(tBu_2Cp)(NMe_2)_3$];

optionally a step b') of vaporizing at least one $M^2$ [metal] containing precursor[, $M^2$ being as hereinabove defined,] to form an optional second gas phase [metal] $M^2$ source;

a step c) of introducing said first gas phase [metal] $M^1$ source and said optional second gas phase [metal] $M^2$ source[,] in the reaction chamber, in order to provoke their contact with said substrate, to generate [the] deposition of [a metal containing] *the* dielectric film comprising [a] *the* compound of the formula (I) [as hereinbefore defined,] on said substrate.

3. The method of claim 1, wherein the $M^2$ [metal] containing precursor[,] is selected from the group consisting of: silicon derivatives or their germanium homologues; silanol derivative of the formula $(III_2)$:

$$Si(OH)_x(OR^4)_{4-x} \quad (III_2)$$

wherein: 1≤x≤3 and $R^4$ represents a linear or branched alkyl group, having 1 to 6 carbon atoms;
aminosilane derivative of the formula $(III_3)$:

$$SiH_x(NR^5R^6)_{4-x} \quad (III_3)$$

wherein[:]*;* 0≤x≤3 and $R^5$ and $R^6$ are identical or different and independently represents an hydrogen atom or a linear or branched alkyl having 1 to 6 carbon atoms;
aluminum derivatives;
amidoalane of the formula $(IV_2)$:

$$AlR^{11}_x(NR^{12}R^{13})_{3-x} \quad (IV_2)$$

wherein: 0≤x≤3 and $R^{12}$ and $R^{13}$ identical or different, represent an hydrogen atom or a linear or branched alkyl having 1 to 6 carbon atoms, and $R^{11}$, identical to or different from $R^7$ and, represents an hydrogen atom or a linear or branched alkyl having 1 to 6 carbon atoms;
tantalum derivatives;
Niobium derivatives;
lanthanide derivatives;
divalent metal derivatives;
and other metal derivatives.

4. The method of claim 3, wherein the [metal containing] dielectric film comprises a compound of the formula $(I_3)$:

$$(M^1_{1-a}M^2_a)O_b \quad (I_3)$$

corresponding to the formula (I), wherein 0≤a≤1 and c=0, wherein the $M^2$ [metal] containing precursor is selected from the silicon derivatives or their germanium homologues, the tantalum derivatives, lanthanide derivatives, or the magnesium derivatives [as hereabove defined].

5. The method of claim 3, wherein the [metal containing] dielectric film comprises a compound of the formula $(I_4)$:

$$(M^1_{1-a}M^2_a)O_bN_c \quad (I_4)$$

corresponding to the formula (I), wherein 0≤a≤1 and 0≤c≤0.5, wherein the $M^2$ [metal] containing precursor is selected from the silicon derivatives or their germanium homologues, the tantalum derivatives, lanthanide derivatives, or the magnesium derivatives [as hereabove defined,] and at least one oxygen containing precursor and at least one nitrogen containing precursor is introduced into the [reactor] *reaction chamber*.

6. The method of claim 3, wherein the silicon derivatives or their germanium homologues are selected from the group consisting of [disiioxane] *disiloxane*, digermoxane, trisilylamine, trigermylamine, disilane, digermane, trisilane, trigermane, alkoxysilane having the formula $SiH_x(OR^3)_{4-x}$, and alkoxygermane having the formula $GeH_x(OR^3)_{4-x}$, wherein[:] 0≤x≤3 and $R^3$ represents a linear or branched hydrocarbon group having 1 to 6 carbon atoms.

15. The method of claim 3, wherein the $M^2$ [metal] containing precursor is a hafnium derivative.

16. The method of claim 1, which further comprises:
[A] *a* step d), wherein the at least one *liquid* $M^1$ [metal] containing precursor and optionally the at least one $M^2$ [metal] containing precursor, is mixed to at least one reactant species prior to step c).

17. The method of claim 1, which further comprises:
a step d') wherein the at least one *liquid* $M^1$ [metal] containing precursor and optionally the at least one $M^2$ [metal] containing precursor, is mixed to at least one reactant species in the reaction chamber.

18. The method of claim 1, wherein the [metal containing] dielectric film comprises a compound of the formula (I₁):

$$M^1O_2 \quad (I_1)$$

corresponding to the formula (I), wherein a=0, b=2 and c=0.

19. The method of claim 1, wherein the [metal containing] dielectric film comprises a compound of the formula (I₂):

$$M^1O_bN_c, \quad (I_2)$$

corresponding to the formula (I), wherein a=0, 1.5≤b≤2.5 and 0<c≤0.5.

20. The method of claim 1, wherein the at least one *liquid* $M^1$ [metal] containing precursor is $ZrCp(NMe_2)_3$.

21. The method of claim 1, wherein the at least one *liquid* $M^1$ [metal] containing precursor is $Zr(MeCp)(NMe_2)_3$.

22. The method of claim 1, wherein the at least one [M metal] *liquid $M^1$ containing* precursor is $Zr(EtCp)(NMe_2)_3$.

23. The method of claim 1, further comprising introducing a reactant species in the reaction chamber, the reactant species selected from the group consisting of oxygen ($O_2$), ozone ($O_3$) moisture ($H_2O$), hydrogen peroxide ($H_2O_2$), plasma generated radicals thereof, and mixtures thereof.

24. The method of claim 23, wherein the reactant species is ozone.

25. The method of claim 23, wherein the liquid $M^1$ containing precursor and the reactant species are introduced sequentially in an atomic layer deposition process.

26. The method of claim 25, wherein the dielectric film is a capacitor dielectric film used in CMOS architecture or DRAM applications.

27. The method of claim 3, wherein the lanthanide derivatives is an yttrium derivative with a beta-diketonate ligand or a cyclopentadienyl ligand optionally substituted with one or several linear or branched alkyl groups having 1 to 6 carbon atoms.

28. A method of manufacturing a $ZrO_2$ high-k capacitor dielectric film for CMOS or DRAM architecture, the method comprising:
vaporizing a liquid Zr-containing precursor to form a gas phase Zr source, the liquid Zr-containing precursor selected from the group consisting of $Zr(MeCp)(NMe_2)_3$, $Zr(EtCP)(NMe_2)_3$, $ZrCp(NMe_2)_3$, $Zr(MeCp)(NEtMe)_3$, $Zr(EtCp)(NEtMe)_3$, $ZrCp(NEtMe)_3$, $Zr(MeCp)NEt_2)_3$, $Zr(EtCp)(NEt_2)_3$, $ZrCp(NEt_2)_3$, and combinations thereof; and
introducing the gas phase Zr source and a reactant species into a reaction chamber containing a substrate to deposit the $ZrO_2$ high-k capacitor dielectric film on the substrate, the $ZrO_2$ high-k dielectric film forming part of the CMOS or DRAM architecture.

29. The method of claim 28, wherein the liquid Zr-containing precursor is selected from the group consisting of $ZrCp(NMe_2)_3$, $Zr(MeCp)(NMe_2)_3$, and $Zr(EtCp)(NMe_2)_3$.

30. The method of claim 29, wherein the liquid Zr-containing precursor is $ZrCp(NMe_2)_3$.

31. The method of claim 29, wherein the liquid Zr-containing precursor is $Zr(MeCp)(NMe_2)_3$.

32. The method of claim 29, wherein the liquid Zr-containing precursor is $Zr(EtCp)(NMe_2)_3$.

33. The method of claim 28, wherein the reactant species is selected from the group consisting of oxygen ($O_2$), ozone ($O_3$), moisture ($H_2O$), hydrogen peroxide ($H_2O_2$), plasma generated radicals thereof, and mixtures thereof.

34. The method of claim 33, wherein the reactant species is ozone.

35. The method of claim 33, wherein the liquid Zr-containing precursor and the reactant species are introduced sequentially in an atomic layer deposition process.

\* \* \* \* \*